United States Patent [19]

Cartwright

[11] 4,050,944

[45] Sept. 27, 1977

[54] GROUND MARKING FOAM

[75] Inventor: Dwayne L. Cartwright, Dallas, Tex.

[73] Assignee: Holloway Farm Supply, Inc., Whitewright, Tex.

[21] Appl. No.: 660,765

[22] Filed: Feb. 23, 1976

[51] Int. Cl.$^2$ ............................................. B01J 13/00
[52] U.S. Cl. ..................................... 106/19; 252/307; 252/311; 252/542; 252/550
[58] Field of Search ................... 106/19; 252/307, 311, 252/531, 542, 550

[56] References Cited

U.S. PATENT DOCUMENTS

| | | | |
|---|---|---|---|
| 3,609,074 | 9/1971 | Rainaldi et al. | 252/307 |
| 3,713,404 | 1/1973 | Lavo et al. | 252/307 |
| 3,914,185 | 10/1975 | Inamorato | 252/307 |
| 3,956,164 | 5/1976 | Walker et al. | 252/180 |
| 3,959,160 | 5/1976 | Horsler et al. | 252/307 |

Primary Examiner—Lorenzo B. Hayes

Attorney, Agent, or Firm—Peter J. Murphy

[57] ABSTRACT

A composition for producing foam is in the form of a concentrate, to be extended or diluted at the point of use in the ratio of about 1 part concentrate to 50 to 80 parts water. The concentrate includes, as principal ingredients, a surfactant functioning as a foam producing ingredient comprising about 5 to 12 percent of the concentrate, a foam stabilizing ingredient to improve the stability or longevity of the foam comprising about 1 to 10 percent of the concentrate; and water as a diluent comprising about 70 to 90 percent of the concentrate. Secondary or optional components of the concentrate may include a water softening ingredient comprising about 0.1 to 5 percent of the concentrate, a buffering agent for stabilizing the pH of the concentrate comprising about 1 to 10 percent of the concentrate, a viscosity reducing ingredient comprising about 1 to 15 percent of the concentrate, and a water soluble coloring ingredient or dye.

7 Claims, 1 Drawing Figure

GROUND MARKING FOAM

BACKGROUND AND SUMMARY OF THE INVENTION

This invention relates to a composition for producing foam, for use as a ground market particularly for agricultural use; and more particularly to a composition and the use thereof to produce a stable foam to provide markings on the ground, in connection with the application of crop control chemicals.

In the application of liquid crop control chemicals to large acreage areas, the equipment used includes spray booms of substantial transverse length, up to sixth feet for example. From the standpoint of effective application of the control chemicals, it is important that no areas of the field be missed; and from the standpoint of efficient and economic application of the chemicals, it is important that the swathes traversed by the spray boom do not overlap each other. To avoid the above mentioned "missed areas" or "overlaps" the spraying equipments have been adopted to provide some form of marker, which marks at least one edge of the swath traversed by the spray boom, which marks can be used as a guide by the same equipment after lapping the field, for example, or by a following piece of equipment which traverses the adjacent swath. To be truly effective, the compositions used for such marking must be stable for a sufficient period of time to allow the equipment to lap the field for example, and the marking material must be stable for varying conditions of the soil and of the ambient atmosphere. Desirably the marking material should remain stable for at least thirty minutes. It should be stable over a range of soil temperatures and over a range of deggree of soil alkalinity. It should also remain stable for the desired period for both low and high humidity conditions, and for conditions of relatively high wind velocity. There has been a need for any years for reliable and economic ground marking systems, for this described use.

Various types of dye markers have been used in the past, and some are effective from the standpoint of an effective and stable mark. One disadvantage of dye markers is that they are quite costly, and another disadvantage is that they are messy from the standpoint of the equipment and from the standpoint of the person and clothing of the operatiors of the equipment.

While various commercial soaps and detergents have been used for marker foams, a major fault of soap markers is the short life of the mark, and the fact that it has little resistance to wind or temperatures and can only be used on a virtually windless day.

A principal object of this invention is to provide a composition for producing a foam ground marker, which is both reliable and economical.

A further object of this invention is to provide a composition for mixture with water, to produce a ground marking foam which will remain stable for various conditions of soil and atmosphere for a significant period of time.

Another object of this invention is to provide a composition for producing a ground marking foam, wherein the cost of application is only a fraction of the cost of dye type compositions for the same purpose.

Another object of this invention is to provide a composition in concentrate form, for admixture with water in the ratio of about 1 part concentrate to 50 to 80 parts of water to produce a reliable and inexpensive ground marking foam.

These and other objects are accomplished in a composition in the form of a concentrate which is effective for producing a ground marking foam when subsequently extended with water in the ratio of 1 part concentrate to about 50 to 80 parts water by volume. The principal ingredients of the concentrate are: a foam producing ingredient in the form of a surfactant comprising from 3 to 20 percent by weight: a foam stabilizing ingredient comprising from 1 to 10 percent by weight; and water as a diluent comprising from 70 to 90 percent by weight. The foam producing ingredient is a compound selected from a group consisting of a fatty alcohol sulfate, an ethoxylated fatty acid sulfate, fatty alcohol sarcosinates, and primary and secondary alkanolamide sulfosuccinates, and salts of said compounds. The foam stabilizing ingredient is a compound selected from a group consisting of high molecular weight alcohols including laruic ($C_{12}$), myristic ($C_{14}$), palmitic ($C_{16}$), a betaine derivative of carboxylic and dicarboxylic acids, the salt of said betaine derivative, a fatty acid dimethylamine oxide, and an amidoalkyl amine oxide.

The novel features and the advantages of the invention, as well as additional objects thereof, will be understood more fully from the following description.

DRAWING

FIG. 1 is a diagrammatic and schematic illustration of a spraying vehicle and associated foam generating and dispensing system.

DESCRIPTION OF THE PREFERRED EMBODIMENTS

Figure 1:
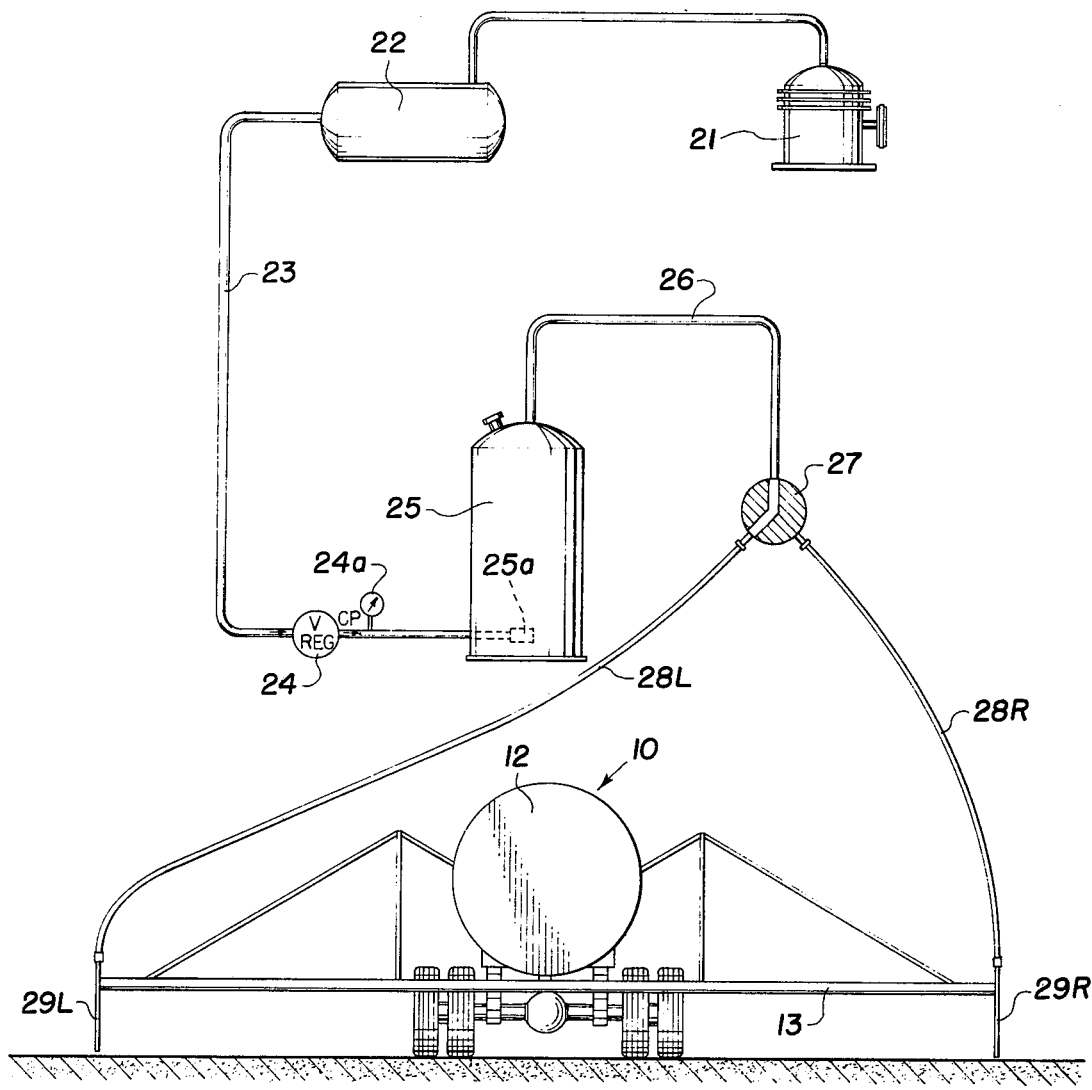

One aspect of this invention is a composition or mixture of certain chemical components with water, initially formulated as a concentrate, for producing a stable foam at a later time when the concentrate is extended or further diluted with an additional quantity of water. Another aspect of the invention is the use of the concentrate, or the method of using the concentrate, to generate and dispense the ground marking foam, the foam having desired properties for this use.

In the following discussion of the ingredients of the concentrate or other composition, the references to percentage of ingredients is by weight, unless otherwise specifically indicated.

Referring to the composition aspect of the invention, the primary ingredients of the concentrte are: (1) a foam producing ingredient which is in the form of a surfactant or surface active agent; (2) a foam stabilizing ingredient, having the capability to enhance the stability and longevity of the produced foam under ambient conditions, and water as a diluent.

Secondary ingredients of the composition are those which may be added to the basic ingredients to improve the properties of the composition for certain conditions of either the ambient atmosphere or the soil. Such secondary ingredients may include: (1) a water softening ingredient to control water hardness due to calcium and magnesium content of the water; (2) a viscosity reducing ingredient to improve the handling of the concentrate prior to its being extended; (3) a buffering ingredient for stabilizing the pH of the concentrate to compensate for different conditions of soil acidity or alkalinity; and (4) a coloring ingredient or dye.

Preferred anionic surfactants, which may serve as the foam producing ingredient, include sodium lauryl sulfate, other fatty alcohol sulfates, ethyoxylated fatty acid sulfates, fatty alcohol sarcosinates, and primary and secondary alkanolamide sulfosuccinates. Also to be included are the corresponding salts of these aforementioned compounds. Preferably the amount of foam producing agent in the concentrate is in the range of about 5 to 12 percent, but may be effective in a range of from 3 to 20 percent. Desirable characteristics of the foam produced is that it be sufficiently dense to resist dissipation due to elevated wind velocity, that the walls of the foam bubbles have sufficient strength and resiliency to resist deterioration under ambient conditions.

A preferred form of foam stabilizing ingredient for the concentrate is either a nonionic, cationic, and/or amphoteric surfactant. This ingredient may be, for example, a betaine derivative or carboxylic and dicarboxylic acids, such as n-lauryl betaine, or their corresponding salts. It may also be a fatty acid dimethylamine oxide or fatty acid amidoakyl amine oxide. The amount of this foam stabilizer in the concentrate is preferably in the range of 1 to 10 percent. Since various ambient temperature conditions will prevail in the geographical areas where the composition is to be used, which will of course effect the soil substrate temperatures, the concentrate foam stabilizing ingredient may desirably serve to increase the elasticity of the bubble wall strength to better resist expansion of the bubbles resulting from expansion of the entrapped air or gas when the temperature increases upon contact with the ground. Ingredients which are suitable for this purpose include: various high molecular weight alcohols such as lauric ($C_{12}$), myristic ($C_{14}$), palmitic ($C_{16}$); and mixtures of such alcohols. Another desirable property of the foam stabilizing ingredient is that it enhance the foam producing ability of the form producing ingredient.

A third basic ingredient is the diluent, water; and this is included in the concentrate preferably in the range of about 70 to 90 percent.

Since foam is often effected by the presence of polyvalent metal ions, such as calcium and magnesium ions, which are present in the water ingredient, it is often desirable to include in the concentrate some ingredient for complexing these metallic ions and thus improving foaming properties, i.e. a water softening ingredient. Such ingredient may be a sequestering phosphate such as sodium tripolyphosphate or sodium hexametaphosphate, or may be a chelating agent such as one of the various salts of ethylenediamine tetraacetic acid or the like. A preferred ingredient is tetrasodium salt of ethylenediamine tetraacetic acid.

Since soil conditions may vary from acid to alkaline, the foam that the concentrate produces must be stable over a wide range of soil alkalinity conditions. This stability may be accomplished by incorporating buffering agents into the concentrate to stabilize the pH of the concentrate. Typical buffering agents include: (1) a weak acid and a salt of a weak acid; (2) a mixture of a weak acid with its normal salt; (3) or a mixture of two salts of weak acids. One example of a suitable buffering agent is $NaH_2PO_4/Na_2HPO_4$. Another example is a mixture of acetic acid and sodium acetate. A further example is a mixture of boric acid and sodium borate.

For certain uses of the foaming concentrate, it may be desirable to add color to the ultimate foam. One reason may be to provide better visibility of the marking foam in relation to the particular color of the soil. Another reason may be to provide better visibility where the marking foam is used over snow for example. A further reason may be simply to provide aesthetic appeal to the foam product, more applicable when the marking foam is used in non-agricultural situations. A suitable dye for this purpose may include a dyestuff whose chromophore is one of the various groups such as nitro (—$NO_2$), nitroso (—NO), oxyazine

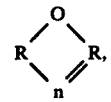

oxyketone

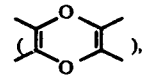

pyronine

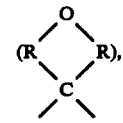

thiazaine

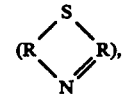

or triphenylmethane

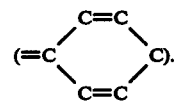

A viscosity reducing ingredient may be desirable to reduce the viscosity of the concentrate, in order to improve handling, without substantially increasing the bulk of the concentrate. The viscosity of the concentrate may of course be reduced with additional water; however this would increase the manufacturing and handling costs by increasing the amount, bulk and weight, without having any other substantial benefit, since the concentrate will be extended with additional water at the point of use. Isopropyl alcohol is a preferred viscosity reducing agent; and this may be included in the concentrate in an amount of about 5% for example. Effective viscosity reduction may be accomplished by including isopropyl alcohol in the concentrate within the range of 1% to 15%. Where isopropyl alcohol is used as viscosity reducer, it may also perform the function of reducing the freezing temperature of the composition, which may be desirable from the standpoint of packaging and shipping during the winter months in colder climates. Other lower molecular weight alcohols such as ethanol, methanol, n-propanol, may likewise be used.

The following are examples of concentrate compositions according to the invention; and these concentrate compositions are intended to be further extended at the point of use by further mixture with water as indicated. Example 1 is the preferred formulation.

Example 1

| | | |
|---|---|---|
| Water Softener | Tetrasodium salt of ethylenediamine tetraacetic acid $(CH_2COONa)_4NCH_2CH_2N$ | 2.0% |
| Foam Producer | Sodium Lauryl Sulfate $C_{11}H_{23}CH_2OSO_3Na$ | 12.0% |
| Foam Stabilizer | N-Lauryl Betaine $C_{11}H_{23}CH_2N(CH_3)_2CH_2COONa$ | 4.0% |
| Viscosity Reducer | Isopropyl Alcohol $(CH_3)_2CHOH$ | 5.0% |
| Diluent | Water $H_2O$ | 77.0% |

Concentrate to be extended with additional water in a ratio of about 80 parts water to 1 part concentrate.

Example 2

| | | |
|---|---|---|
| Foam Producer | A mixture of fatty alcohol sulfate and a primary or secondary alkanolamide sulosuccinate | 15.0% |
| Foam Stabilizer | n-dodecanol | 0.5% |
| Buffering Agent | Boric acid/Sodium borate mixture | 0.5% |
| Diluent | Water | 84.0% |

Concentrate to be extended with additional water in a ratio of about 50 parts water to 1 part concentrate

Example 3

| | | |
|---|---|---|
| Foam Producer | A mixture of fatty alcohol sulfate and a primary or secondary alkanolamide sulfosuccinate | 15.0% |
| Foam Stabilizer | fatty acid amidoalkyl amine oxide | 2.0% |
| Water Softener | Sodium hexametaphosphate and/or sodium or potassium salt of ethylenediamine tetraacetic acid | 4.0% |
| Diluent | Water | 79.0% |

Concentrate to be extended with additional water in a ratio of about 50 parts water to 1 part concentrate

Example 4

| | | |
|---|---|---|
| Foam Producer | A fatty alcohol sulfate and/or fatty alcohol ether sulfate | 15.0% |
| Foam Stabilizer | Betaine derivative of a mono or dicarboxylic acid | 5.0% |
| Water Softener | Sodium hexametaphosphate | 2.0% |
| Diluent | Water | 78.0% |

Concentrate to be extended with additional water in a ratio of about 50 parts water to 1 part concentrate.

For the formulation of a concentrate according to the Example 1 for example, an appropriate batch size is determined and the amounts of the various ingredients are carefully weighed. The mixing tank is first charged with the water ingredient, and this is maintained at a temperature of between 70° F. and 90° F. to facilitate the mixing of the balance of the ingredients. The water softening ingredient is added next, also to facilitate the mixing of the subsequently added ingredients to the water. The foam producing ingredient is then added, with the solution being gently and thoroughly agitated to keep air entrapment and foaming to a minimum, and yet to assure a homogeneous product. After this mixing is completed, the foam stabilizing ingredient is added, followed by the addition of the viscosity reducing ingredient.

For other formulations, the buffering agent would preferably be added following the addition of the foam stabilizing agent; and normally the coloring ingredient would be the last ingredient to be added.

With reference to the drawing, a typical spraying vehicle, with which the above described composition may be used, consists of a conventional two axel truck chassis 10 having a forward cab, a large tank 12 behind the cab for the crop control chemical, and an elongated horizontal spray boom 13 supported at the rear of the chassis. Foam dispensing apparatus for such vehicle may include the following components: an engine driven air compressor 21 and associated air supply tank 22; a closed foam generating tank 25; a pressure regulator 24 in the conduit 23 coupling the air supply tank and foam generating tank, a restricted foam outlet conduit 26 for conducting the foam from the top of the foam generating tank to a selector valve 27; the selector valve 27 directing the foam alternatively to left or right boom conduits 28L and 28R, for carrying the foam to respective left and right boom drop hoses 29L and 29R, at the ends of the spray boom 13.

If the spraying vehicle includes an air brake system, appropriate components of the air brake system may serve as the above mentioned air compressor 21 and air supply tank 22. If not, a suitable air compressor may be provided to be driven by the vehicle engine; and an air supply tank in the form of a 100 psi pressure vessel may be provided. The compressor is preferably equipped with a governor to maintain about 100 psi in the air supply tank.

The air supply conduit 23 is preferably a ⅜ inch hose; and this is connected to a suitable air discharge tip or nozzle 25a associated with the foam generating tank. For convenience of control, the pressure regulator 24 and associated pressure gauge 24a, on the downstream side of the regulator, are mounted within the cab for monitoring and adjusting the pressure within the foam generating tank.

The foam generating tank 25 is preferably a tall, slender pressure vessel, having a 75 psi working pressure for example, and which may be mounted at any convenient location on the spraying vehicle 10. The tank would have a fluid level indicator to maintain a chamber t the tope of the tank for the collection and discharge of foam produced. The foam outlet conduit 26 is preferably a ¾ inch hose, and the boom conduits 28L and 28R for carrying the foam from the selector valve alternatively to the left or right boom are preferably ¾ inch hoses. The boom drop hoses 29L and 29R, which are preferably a minimum of 1 inch hoses, are vertical hoses which extend downwardly from the booms to the ground, and may drag on the ground, for directly depositing the foam onto the ground.

In the operation of the foam dispensing apparatus, the pressure in the foam generating tank may be maintained at from 20 psi to 40 psi for example, with the air pressure effecting flow of foam from the tank chamber to the drop hoses, with the desired flow of air through the foam generating tank being maintained to produce the foam as needed.

The vehicle operator controls the manner in which the foam is dispensed by adjusting the pressure maintained in the foam generating tank. Through maintenance of a higher pressure, the foam will be dispensed from the boom drop hoses in a continuous stream. By maintaining a lower pressure, and with the boom drop hoses being larger than the boom conduits, the foam can be controlled to collect in the boom drop hoses to be dispensed in intermittent blobs. The operator then, has wide control of the manner and volume in which the foam is deposited on the ground.

What has been described is a composition in the form of a concentrate which is particularly effective for the production of a ground marking foam when later mixed or extended with additional quantities of water and air is passed through the extended composition. The composition has the characteristic to produce foam of the desired density and stability to remain intact on the ground during ambient conditions of temperature nd wind velocity, for example, which conditions would tend to quickly dissipate foam produced by commercial soaps or detergents, for example. The foam produced has a density and resiliency to resist dissipation due to elevated wind velocities, thereby enabling chemical spraying of crops and fields under such conditions; wherein with the use of foams produced by commercial soaps or detergents the spraying could only be done on a virtually calm day. Elevated ground temperature effects rapid expansion of the foam bubbles, when the foam contacts the ground, due to increase in temperature of the foam; and the bubble walls of the produced foam have the elasticity to withstand substantial enlargement without rupture.

The composition described will produce such foam, which will remain stable under these conditions not only for a relatively few minutes but for an extended period of 30 minutes or more to allow ample time for the spraying vehicles to either lap a field for example or to traverse swathes of a field which are of substantial length. The composition described can be produced economically, is produced in concentrate form to reduce shipping costs to the point of use, and is then extended with further quantities of water at the point of use for the production of the desired foam. The ground marking foam applied in this manner, is applied at a much lower cost per acre than dye type marker materials which were required previously to ensure that the mark on the ground would have sufficient stability in terms of time.

What is claimed is:

1. A composition effective for producing an agricultural ground marking foam by passing air therethrough, comprising a concentrate to be further extended with water in the ratio of about 1 part concentrate to 80 parts water, by volume; said concentrate consisting essentially of:

sodium lauryl sulfate functioning as a foam producing ingredient; said foam producing ingredient comprising of 5 to 12 percent of the concentrate by weight;

n-lauryl betaine functioning as a foam stabilizer; said foam stabilizer comprising 1 to 10 percent of said concentrate by weight;

and water functioning as a diluent; said diluent comprising 70 to 90 percent of said concentrate by weight.

2. A composition as set forth in claim 1 wherein said concentrate further consists of:

tetrasodium salt of ethylenediamine tetraacetic acid functioning as a water softener; said water softener comprising 0.1 percent to 5 percent of said concentrate by weight;

isopropyl alcohol functioning as a viscosity reducing agent; said viscosity reducing agent comprising 1 percent to 15 percent of said concentrate by weight.

3. A composition as set forth in claim 2 wherein said foam producing ingredient comprises about 12 percent of said concentrate by weight; wherein said foam stabilizer ingredient comprises about 4 percent of said concentrate by weight; wherein said water softening ingredient comprises about 2 percent of said concentrate by weight; wherein said viscosity reducing ingredient comprises about 5 percent of said concentrate by weight; and wherein said water diluent comprises about 77 percent of said concentrate by weight.

4. A method for producing a foam, effective to be deposited on the ground as a ground marking material to guide the application by swaths of agricultural chemicals, which method comprises preparing a concentrate composition consisting essentially of:

sodium lauryl sulfate functioning as a foam producing ingredient; said foam producing ingredient comprising of 5 to 12 percent of the concentrate by weight;

n-lauryl betaine functioning as a foam stabilizer; said foam stabilizer comprising 1 to 10 percent of said concentrate by weight;

and water functioning as a diluent; said diluent comprising 70 percent to 90 percent of said concentrate by weight;

extending said concentrate composition with water in a ratio of about 1 part concentrate to 80 parts water;

and passing air through said extended concentrate.

5. A method as set forth in claim 4 wherein said concentrate composition further consists of:

tetrasodium salt of ethylenediamine tetraacetic acid functioning as a water softener; said water softener comprising 0.1 percent to 5 percent of said concentrate by weight;

isopropyl alcohol functioning as a viscosity reducing agent; said viscosity reducing agent comprising 1 percent to 15 percent of said concentrate by weight.

6. A method as set forth in claim 5 wherein the weight percentages of said concentrate composition ingredients are:

sodium lauryl sulfate, about 12% n-lauryl betaine, about 4% tetrasodium salt of ethylenediamine tetraacetic acid about 2% isopropyl alcohol about 5% water about 77%.

7. A method as set forth in claim 4 wherein said air is passed through said extended concentrate at a pressure of about 20 psi to 40 psi.

* * * * *

UNITED STATES PATENT OFFICE
CERTIFICATE OF CORRECTION

PATENT NO. : 4,050,944
DATED : September 27, 1977
INVENTOR(S) : Dwayne L. Cartwright It is certified that error appears in the above-identified patent and that said Letters Patent are hereby corrected as shown below:

Column 1, line 7    change "market" to --marker--
Column 1, line 14   change "sixth" to --sixty--
Column 1, line 40   change "any" to --many--
Column 2, line 21   change "laruic" to --lauric--
Column 6, line 38   change "t" to --at--
Column 6, line 39   change "tope" to --top--
Column 7, line 6    change "nd" to --and--

Signed and Sealed this

Third Day of January 1978

[SEAL]

Attest:

RUTH C. MASON
Attesting Officer

LUTRELLE F. PARKER
Acting Commissioner of Patents and Trademarks